United States Patent

Degner et al.

[11] 4,350,641
[45] Sep. 21, 1982

[54] 4-TERT.-BUTOXYPHENYLGLYCINONITRILE AND THE PREPARATION OF D-(−)- AND L-(+)-4-HYDROXYPHENYLGLYCINE

[75] Inventors: Dieter Degner, Dannstadt-Schauernheim; Hans J. Pander, Roedersheim-Gronau; Hardo Siegel, Speyer, all of Fed. Rep. of Germany

[73] Assignee: BASF Aktiengesellschaft, Fed. Rep. of Germany

[21] Appl. No.: 221,540

[22] Filed: Dec. 31, 1980

[30] Foreign Application Priority Data

Jan. 25, 1980 [DE] Fed. Rep. of Germany ....... 3002543

[51] Int. Cl.³ .................. C07C 121/80; C07C 99/10; C07C 101/30
[52] U.S. Cl. ................. 260/465 E; 562/401; 562/444
[58] Field of Search ............ 260/465 E; 562/401, 562/444

[56] References Cited

U.S. PATENT DOCUMENTS

| 4,072,698 | 2/1978 | Hylton et al. ................ 260/465 E |
| 4,233,456 | 11/1980 | Schmand et al. ................ 562/401 |
| 4,238,507 | 12/1980 | Vmezawa et al. ........... 260/465 E X |

FOREIGN PATENT DOCUMENTS 1060 8/1978 European Pat. Off. ........ 260/465 E

*Primary Examiner*—Dolph H. Torrence

*Attorney, Agent, or Firm*—Keil & Witherspoon

[57] ABSTRACT

4-Tert.-butoxyphenylglycinonitrile (I)

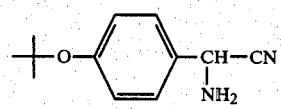

and a process for the preparation of D-(−)-4-hydroxyphenylglycine (IIa) and L-(+)-4-hydroxyphenylglycine (IIb)

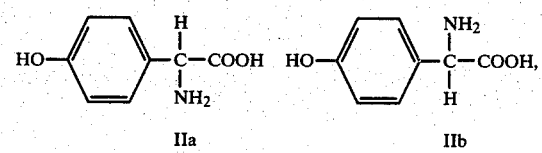

wherein compound I is reacted in a conventional manner, in alcoholic solution and in the presence of a carbonyl compound, with about the equimolar amount of L-(+)-tartaric acid or D-(−)-tartaric acid and the D-(−)-I-L-(+)-tartrate or L-(+)-I-D-(−)-tartrate thereby obtained in crystalline form is converted to IIa or IIb respectively in aqueous acid solution at 20°–110° C. by splitting off the L-(+)-tartaric acid or D-(−)-tartaric acid, hydrolyzing the nitrile group and hydrolytically splitting off the tert.-butyl group.

3 Claims, No Drawings

4-TERT.-BUTOXYPHENYLGLYCINONITRILE AND THE PREPARATION OF D-(−)- AND L-(+)-4-HYDROXYPHENYLGLYCINE

The present invention relates to the novel compound 4-tert.-butoxyphenylglycinonitrile (I)

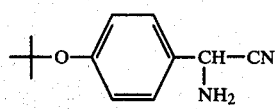

and an improved process, starting from this compound, for the preparation of D-(−)-4-hydroxyphenylglycine (IIa) and L-(+)-4-hydroxyphenylglycine (IIb)

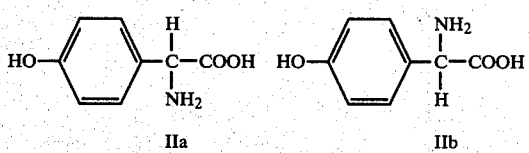

European Laid-Open Application No. 0.001,060 discloses that the opticalisomers of a phenylglycine (IIc)

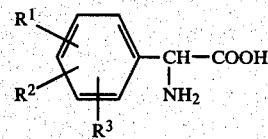

wherein $R^1$, $R^2$ and $R^3$ are hydrogen or, inter alia, hydroxyl, alkyl or alkoxy, may be prepared by reacting the corresponding DL-phenylglycinonitrile Ic

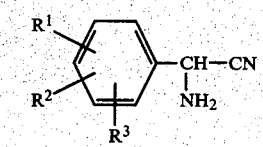

in solution, preferably in methanol, and in the presence of a carbonyl compound, with L-(+)-tartaric acid, separating off the more sparingly soluble diastereomeric L-(+)-tartrate which hereupon crystallizes out, and thereafter hydrolyzing this compound to the acid IIc. During the formation of the tartrate, the presence of the carbonyl compound causes racemization of the optical isomer of Ic which forms the more easily soluble diastereomeric tartrate, whilst the isomer which forms the more sparingly soluble tartrate escapes racemization as a result of crystallizing out. This means that, at least theoretically, the whole of the DL-Ic is converted to the more sparingly soluble L-(+)-tartrate (either of D-Ic or of L-Ic). The 4-hydroxy derivative of Ic in this way gives compound IIa, which is very important for the preparation of semi-synthetic antibiotics.

The total synthesis of IIa, which starts from 4-hydroxybenzaldehyde and of which the component steps are known from the prior art discussed in European Laid-Open Application No. 0,001,060, namely

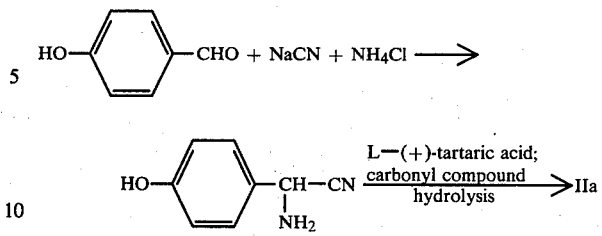

is however economically unsatisfactory because the yields are insufficient.

For this reason it has hitherto been preferred to start from the methyl ether of 4-hydroxybenzaldehyde and cleave the ether again, in the last step of the synthesis, to give the free hydroxyl compound IIa. However, since the reaction conditions required for this purpose are relatively severe, partial racemization of IIa is virtually unavoidable.

It is an object of the present invention to avoid this disadvantage and to make the compound IIa technically more easily, and more cheaply, available. It is a further object to avoid the same disadvantages in the preparation of the antipode compound IIb, which is also an important drug intermediate.

We have found that these objects are achieved and that D-(−)-4-hydroxyphenylglycine (IIa) and L-(+)-4-hydroxyphenylglycine (IIb)

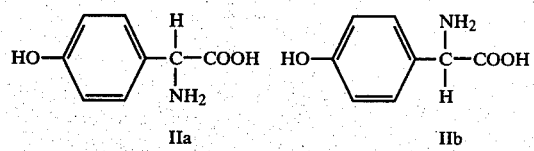

are obtained in an advantageous manner if DL-4-tert.-butoxyphenylglycinonitrile (I)

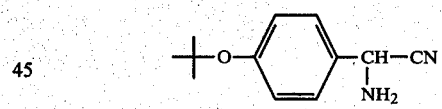

is reacted, in a conventional manner, in alcoholic solution and in the presence of a carbonyl compound, with about the equimolar amount of L-(+)-tartaric acid or D-(−)-tartaric acid and the D-(−)-I-L-(+)-tartrate or L-(+)-I-D-(−)-tartrate thereby obtained in crystalline form is converted to IIa or IIb respectively in aqueous acid solution at 20°–110° C. by splitting off the L-(+)-tartaric acid or D-(−)-tartaric acid, hydrolyzing the nitrile group and hydrolytically splitting off the tert.-butyl group.

Further, we have found that methylglyoxal dimethylacetal (III)

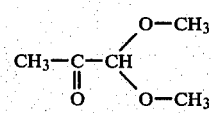

is a particularly suitable carbonyl compound to use in this reaction.

4-TERT.-BUTOXYPHENYLGLYCINONITRILE AND THE PREPARATION OF D-(−)- AND L-(+)-4-HYDROXYPHENYLGLYCINE

The present invention relates to the novel compound 4-tert.-butoxyphenylglycinonitrile (I)

and an improved process, starting from this compound, for the preparation of D-(−)-4-hydroxyphenylglycine (IIa) and L-(+)-4-hydroxyphenylglycine (IIb)

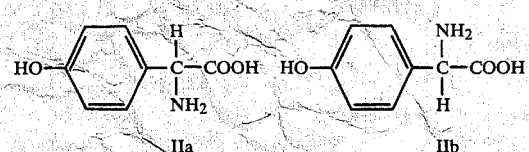

European Laid-Open Application No. 0,001,060 discloses that the opticalisomers of a phenylglycine (IIc)

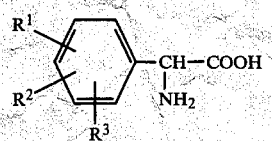

wherein $R^1$, $R^2$ and $R^3$ are hydrogen or, inter alia, hydroxyl, alkyl or alkoxy, may be prepared by reacting the corresponding DL-phenylglycinonitrile Ic

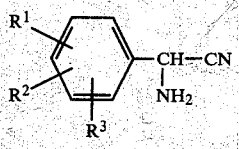

in solution, preferably in methanol, and in the presence of a carbonyl compound, with L-(+)-tartaric acid, separating off the more sparingly soluble diastereomeric L-(+)-tartrate which hereupon crystallizes out, and thereafter hydrolyzing this compound to the acid IIc. During the formation of the tartrate, the presence of the carbonyl compound causes racemization of the optical isomer of Ic which forms the more easily soluble diastereomeric tartrate, whilst the isomer which forms the more sparingly soluble tartrate escapes racemization as a result of crystallizing out. This means that, at least theoretically, the whole of the DL-Ic is converted to the more sparingly soluble L-(+)-tartrate (either of D-Ic or of L-Ic). The 4-hydroxy derivative of Ic in this way gives compound IIa, which is very important for the preparation of semi-synthetic antibiotics.

The total synthesis of IIa, which starts from 4-hydroxybenzaldehyde and of which the component steps are known from the prior art discussed in European Laid-Open Application No. 0,001,060, namely

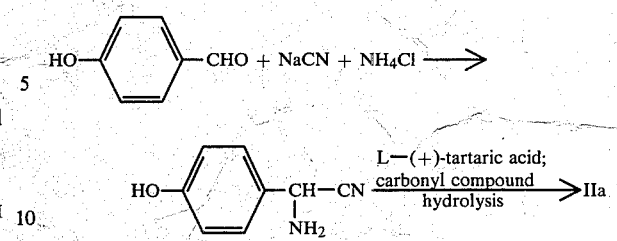

is however economically unsatisfactory because the yields are insufficient.

For this reason it has hitherto been preferred to start from the methyl ether of 4-hydroxybenzaldehyde and cleave the ether again, in the last step of the synthesis, to give the free hydroxyl compound IIa. However, since the reaction conditions required for this purpose are relatively severe, partial racemization of IIa is virtually unavoidable.

It is an object of the present invention to avoid this disadvantage and to make the compound IIa technically more easily, and more cheaply, available. It is a further object to avoid the same disadvantages in the preparation of the antipode compound IIb, which is also an important drug intermediate.

We have found that these objects are achieved and that D-(−)-4-hydroxyphenylglycine (IIa) and L-(+)-4-hydroxyphenylglycine (IIb)

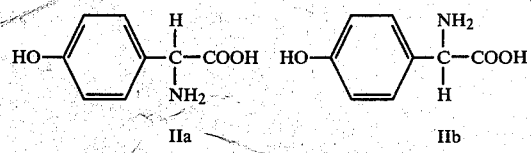

are obtained in an advantageous manner if DL-4-tert.-butoxyphenylglycinonitrile (I)

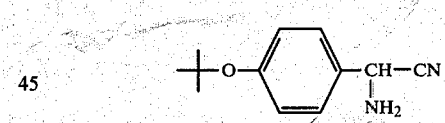

is reacted, in a conventional manner, in alcoholic solution and in the presence of a carbonyl compound, with about the equimolar amount of L-(+)-tartaric acid or D-(−)-tartaric acid and the D-(−)-I-L-(+)-tartrate or L-(+)-I-D-(−)-tartrate thereby obtained in crystalline form is converted to IIa or IIb respectively in aqueous acid solution at 20°–110° C. by splitting off the L-(+)-tartaric acid or D-(−)-tartaric acid, hydrolyzing the nitrile group and hydrolytically splitting off the tert.-butyl group.

Further, we have found that methylglyoxal dimethylacetal (III)

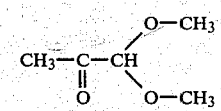

is a particularly suitable carbonyl compound to use in this reaction.

The starting compound DL-I required for the process according to the invention had not previously been disclosed but is obtainable in a conventional manner by reacting 4-tert.-butoxybenzaldehyde with anhydrous hydrogen cyanide and then reacting the product with anhydrous ammonia at from −20° to 30° C.

The subsequent reaction with L-(+)-tartaric acid or D-(−)-tartaric acid, accompanied by stereoisomerization, is carried out in solution in an alcohol, in particular methanol, namely either in methanol alone or, preferably, in a solvent mixture which contains methanol. For example, mixtures with ethyl acetate, benzene, toluene, methylene chloride or dichloroethane, in each case containing from 10 to 80% by volume of methanol, have proved very suitable.

The amount of these solvents used is from about 2 to 8 liters per kg of I.

In principle, suitable carbonyl compounds are all aldehydes and ketones as well as their lower dialkylacetals, provided there is no steric hindrance of the carbonyl group or of the acetal group. Examples of such carbonyl compounds, whose use in the stereoisomerization of phenylglycine, phenylglycine esters, phenylglycinonitrile and their nuclear-substituted derivatives is known, are acetone, benzaldehyde, cyclohexanone, methyl ethyl ketone, n-butyraldehyde and methyl isobutyl ketone.

Particularly good results in respect of a high degree of stereoisomerization are obtained, in the present case, with compound III, which has not previously been proposed for use in the above syntheses. The fact that III is very suitable is particularly surprising since III is a bifunctional carbonyl compound. As it must be assumed that the phenylglycine derivatives react with the carbonyl compounds to form, as intermediates, Schiff bases, which racemize particularly easily, it would have been expected that in the case of bifunctional carbonyl compounds both functional groups would react with the phenylglycine compound, thereby interfering with the racemization mechanism.

In general, preferred amounts of the carbonyl compounds are from 1 to 4 moles per mole of I, but compound III offers the advantage that smaller amounts, from about 0.1 to 0.5 mole, suffice.

The raction, for which the L-(+)-tartaric acid and the DL-I are employed in about equimolar amounts, and which is accompanied by the formation of the solid D-(−)-I-L-(+)-tartrate, in general—ie. in the presence of a carbonyl compound chosen at random-requires from about 2 to 6 hours. If III is used as the carbonyl compound, the reaction time can be reduced to about one hour. The same is of course true of the formation of the optical isomer, namely L-(+)-I-D-(−)-tartrate.

The tartrate which crystallizes out is then separated off and dissolved in dilute aqueous acid, for example dilute hydrochloric acid or sulfuric acid, after which the solution is heated at 20°-110° C. This liberates the tartaric acid, converts the nitrile group to the carboxyl group and hydrolytically splits off the tert.-butyl group, forming tert.-butanol or, for example, tert.-butyl chloride and liberating the free phenolic hydroxyl group of IIa or IIb.

The hydrolysis mixture is then worked up in a conventional manner to give the desired compound IIa or IIb, the yield being about 60-75%, based on I.

EXAMPLE 1

Preparation of (DL)-p-tert.-butoxyphenylglycinonitrile (I)

(a) Preparation of p-tert.-butoxybenzaldehyde-cyanohydrin 1,212 g (6.8 moles) of p-tert.-butoxybenzaldehyde were added, in portions, to a stirred solution of 190 g (7 moles) of anhydrous hydrogen cyanide, 2 g of N,N-dimethylethanolamine as a basic condensing agent, and 400 g of diethyl ether, at 0°-5° C., and the mixture was then kept at −10° C. for one hour. The cyanohydrin, which precipitated as a crystal sludge, was separated off and dried; melting point 73°-74° C.; yield 92%.

(b) Preparation of I

A mixture of 51.3 g (0.25 mole) of the cyanohydrin and 68 g (4 moles) of anhydrous ammonia were stirred for 24 hours in an autoclave at 20°-30° C. This resulted in the formation of I as a crystalline reaction product, of melting point 50°-51° C., the yield being 94%. The crude product, which was accordingly 94% pure, was used, without additional purification, for the subsequent reactions.

EXAMPLE 2

Preparation of the D-(−)-I-L-(+)-tartrate, using acetone as the carbonyl compound 86.8 g (0.42 mole) of (DL)-4-tert.-butoxyphenylglycinonitrile (I), 64 g (0.42 mole) of L-(+)-tartaric acid and 24 g (0.42 mole) of acetone were stirred for 5 hours with a mixture of 175 moles of methanol and 520 ml of ethyl acetate at 40° C. When the mixture had cooled to 20° C., a crystal sludge formed, which was separated off and dried. The yield of tartrate was 78%.

$[\alpha]_D^{20} = +32.0°$ (c=1; H$_2$O); this corresponds to 94% optical purity of the D-(−)-I component of the tartrate.

EXAMPLE 3

Preparation of the D-(−)-I-L-(+)-tartrate, using III as the carbonyl compound

A solution of 102 g (0.5 mole) of I in 490 ml of methylene chloride was mixed with a solution of 75 g (0.5 mole) of L-(+)-tartaric acid and 14.5 g (0.13 mole) of methylglyoxal dimethylacetal, and the mixture was refluxed for two hours and then cooled to 20° C. The yield of the salt which hereupon precipitated was 86%.

$[\alpha]_D^{20} = +32.3°$ (c=1; H$_2$O); this corresponds to 98% optical purity of the D-(−)-I component of the tartrate.

EXAMPLE 4

Preparation of the L-(+)-I-D-(−)-tartrate

This compound was prepared by a method similar to Example 3, from I and D-(−)-tartaric acid; yield 85%.

$[\alpha]_D^{20} = -31.3°$ (c=1; H$_2$O); this corresponds to 95% optical purity of the L-(+)-I component of the tartrate.

EXAMPLE 5

Preparation of D-(−)-4-hydroxyphenylglycine (IIa)

33 g (about 0.2 mole) of the tartrate prepared as described in Example 2 were heated with 150 ml of 20% strength by weight hydrochloric acid, causing tert.- butyl chloride to distil off. After subsequent refluxing for one hour, the reaction mixture was cooled, mixed with active charcoal and filtered.

The filtrate was then brought to pH 6.5-7.0 with 50% strength by weight sodium hydroxide solution, after which the product crystallized out. It was separated off and dried. The yield of IIa was 79%, based on tartrate employed.

$[\alpha]_D^{20} = -151°$ (1 N HCl); this corresponds to 94% optical purity of IIa.

The tartrate prepared as described in Example 3 similarly gave compound IIa in 82% yield and 98% optical purity;

$[\alpha]_D^{20} = -156°$ (1 N HCl).

EXAMPLE 6

Preparation of L-(+)-4-hydroxyphenylglycine (IIb)

This compound was prepared by a method similar to Example 5, from the tartrate obtained in Example 4. The yield was 76% and the optical purity was 95%.

$[\alpha]_D^{20} = +152°$ (1 N HCl).

We claim:

1. 4-tert.-Butoxyphenylglycinonitrile (I).

2. A process for the preparation of D-(−)-4-hydroxyphenylglycine (IIa) and L-(+)-4-hydroxyphenylglycine (IIb)

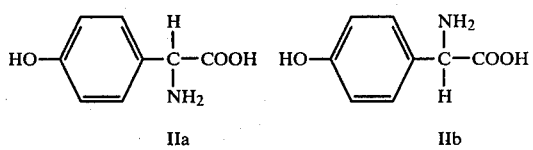

which comprises: reacting DL-4-tert.-butoxyphenylglycinonitrile (I)

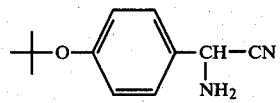

in alcoholic solution and in the presence of a carbonyl compound, with about the equimolar amount of L-(+)-tartaric acid or D-(−)-tartaric acid and the D-(−)-I-L-(+)-tartrate or L-(+)-I-D-(−)-tartrate thereby obtained in crystalline form is converted to IIa or IIb respectively in aqueous acid solution at 20°-110° C. by splitting off the L-(+)-tartaric acid or D-(−)-tartaric acid, hydrolyzing the nitrile group and hydrolytically splitting off the tert.-butyl group.

3. A process as set forth in claim 2, wherein methylglyoxal dimethylacetal (III)

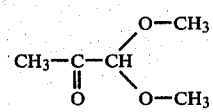

is used as the carbonyl compound.

* * * * *